United States Patent [19]

Greer

[11] 4,258,036

[45] Mar. 24, 1981

[54] COLOR AND GROWTH ENCHANCEMENT OF THE COAST OF FELINES AND CANINES

[76] Inventor: Phyllis T. Greer, 275 Channel Dr., Novato, Calif. 94947

[21] Appl. No.: 69,933

[22] Filed: Aug. 27, 1979

[51] Int. Cl.³ .................... A61K 35/78; A61K 47/00
[52] U.S. Cl. ................................. 424/195; 424/74; 424/360; 424/364
[58] Field of Search ................ 424/74, 195, 360, 364

[56] References Cited

U.S. PATENT DOCUMENTS 3,809,747  5/1974  Toscano ............................. 424/74

FOREIGN PATENT DOCUMENTS

| 73-43850 | 5/1970 | Japan | 424/74 |
| 166227 | 7/1921 | United Kingdom | 424/74 |
| 624624 | 6/1949 | United Kingdom | 424/74 |
| 504536 | 5/1976 | U.S.S.R. | 424/74 |

OTHER PUBLICATIONS

Chem. Abst. vol. 58: 10566, (1963), vol. 32: 1345–1346, (1938).
The Pharmaceutical Recipe Book, pub. by Amer. Pharm. Asso., 2nd Ed., 1936, pp. 325–326.
U.S. Dispensatory, J. B. Lippincott Co., Phila., 24th Ed., 1947, pp. 213–215.
Szabo, Amer. Perf. & Cos., vol. 85, No. 12, Dec. 1970, pp. 39–42.

*Primary Examiner*—Anna P. Fagelson
*Attorney, Agent, or Firm*—Melvin R. Stidham

[57] ABSTRACT

This invention relates to a diet supplement for enhancing the coat of felines and canines. More specifically, this invention relates to a formulation consisting of a primary component, capsicum tetragonum, which is mixed with kelp and a gelatinous material. The formulation is especially useful during those periods of time when the felines or canines shed their coats. The primary effect of this formulation is to enhance the growth of the coat and intensify the color thereof during the life of the feline or canine.

2 Claims, No Drawings

COLOR AND GROWTH ENCHANCEMENT OF THE COAST OF FELINES AND CANINES

CROSS REFERENCE TO RELATED APPLICATION

This application is a substitute for any application Ser. No. 874,240 which was a continuation-in-part of then copending application, Ser. No. 766,603, filed Feb. 7, 1977 both now abandoned.

BACKGROUND OF THE INVENTION

During the normal daily life of most dogs or cats, a small amount of its coat is naturally ejected and is subsequently replaced by a natural processes. However, most dogs or cats have a shedding period wherein most of the coat falls out and is replaced. During this shedding period, the animal appears shaggy, splotchy and generally unkept in appearance.

Much time and effort has been directed to alleviating the problem created by this shedding. In general, there has been proposed essentially two (2) methods of enhancing the growth of the coat during peak shedding periods for the dogs or cats. These methods can be classified as physical and essentially chemical.

The physical method for enhancing the growth of the coat of dogs and cats consists of several approaches. The most widely used approach is to simply brush or pluck the coat and thus stimulate the skin and the fallicles to enhance the growth thereof. Another approach is to add an oil substance to the skin and/or coat to enhance the growth and appearance thereof. Additionally, it has also been the practice to wrap the coat with strips of impervious material, such as waxed paper, foil, etc., to enhance the growth thereof.

The chemical method of enhancing the growth consists of orally administering to the dog or cat a wide variety of materials to enhance the growth and/or appearance of the coat. This includes the administering of vitamins, such as vitamin E, $B_1$ and $B_{12}$ and the like. Another approach has been proposed which consists of adding carbohydrates in any convenient form desirable. Another approach has been to add proteins to the diet of the animal to enhance the growth and/or appearance of the coat. Other approaches have been tried without any notable success.

Each of these methods has had some degree of success, but each lacks the essential feature of fast replacement of the coat lost during the shedding periods of the animal.

DESCRIPTION OF THE INVENTION

In the practice of the present invention, a veterinary diet supplement is provided particularly useful to enhance the color intensity and stimulate the growth of the coat on mammals or avians. Specifically, it has been found in practice that the color is intensified and the growth of the coat is stimulated by the addition of paprika capsicum tetragonum to the diet of the animal. The paprika can be used in any convenient form and includes the stems, pods and seeds or mixtures thereof. As is well understood to culinary artisans, paprika is used primarily as a flavoring and a coloring agent. However, as will be hereinafter specifically set out, paprika greatly enhances the color and the growth of the coat on dogs and cats during normal shedding periods. As is well understood, paprika probably has very little food value in that its vitamin, carbohydrate and protein content is extremely small, indeed, if any at all. Thus, no particular hypothesis can be advanced for the uniqueness in stimulating the growth of the coat and intensifying the color thereof in dogs and cats.

The amount of paprika added to the diet of mammals can range between, by volume, one-fourth (¼) teaspoon to about one (1) teaspoon per ten (10) pounds body weight per day. The amount of paprika added to the diet for proper coat maintenance will range between about one-fourth (¼) to about one-half (½) teaspoon per ten (10) pounds of body weight per day. For poor coat condition and shedding periods, up to about one (1) teaspoon per ten (10) pounds body weight is preferred until the condition is corrected. The particular amount of paprika added to the diet of the mammal will depend on the weight and species thereof. It has been found in practice that there are no side effects with the animals in any way whatsoever, including its breeding ability, reproductive ability, appetite, mental or psychological aspects.

In its most preferred form, the paprika is combined with unrefined kelp and/or a gelatinous material. The kelp most useful with this invention is defined as the Pacific Brown Kelp or the California Kelp which can be obtained at many commercial outlets in the form of dietary supplements. Also, Norwegian kelp can be used. The amount of kelp can range between about 0 and 50% by volume.

The gelatin material usable with the present invention can be selected from a wide variety of materials that are commercially available. Among the many gelatinous materials available are Knox gelatin, 100 Bloom and the like. The amount of gelatin usable for the formulation will range between about 0 and 50% by volume.

In its preferred form, the paprika, kelp and gelatin are mixed together in appropriate amounts and then made into tablets or in capsule form to be orally administered to the mammals or avians. It is to be understood, however, that the formulation can be administered in powder form or can be made into a liquid or syrup.

It has been found in practice that the administration of this formulation does not cause rejection thereof. In fact, the mammals and avians appear to readily eat the formulation however administered.

As has been pointed out previously, the amount of paprika capsicum tetragonum added to the diet will range between one-fourth (¼) teaspoon to about one (1) teaspoon per ten (10) pounds body weight per day, and one-fourth (¼) to about one-half (½) teaspoon is specifically preferred to maintain proper coat. However, in order to be complete, the following formulations are provided:

1. 100% paprika.
2. 90 to 99% paprika, 1 to 10% kelp, 1 to 10% gelatin, preferably kelp and gelatin combined to make 1 to 10% of the total.
3. 80 to 90% paprika, 10 to 20% kelp, 10 to 20% gelatin or kelp and gelatin combined to make 10 to 20% of the total.
4. 70 to 80% paprika, 20 to 30% kelp, 20 to 30% gelatin or kelp and gelatin combined to make 20 to 30% of the total.
5. 60 to 70% paprika, 30 to 40% kelp, 30 to 40% gelatin or kelp and gelatin combined to make 30 to 40% of the total.

6. 50 to 60% paprika, 40 to 50% kelp, 40 to 50% gelatin or kelp and gelatin combined to make 40 to 50% of the total.

7. 40 to 50% paprika, 50 to 60% kelp, 50 to 60% gelatin or kelp and gelatin combined to make 50 to make 50 to 60% of the total.

8. 30 to 40% paprika, 60 to 70% kelp, 60 to 70% gelatin or kelp and gelatin combined to make 60 to 70% of the total. 9. 20 to 30% paprika, 70 to 80% kelp, 70 to 80% gelatin or kelp and gelatin combined to make 70 to 80% of the total. 10. 10 to 20% paprika, 80 to 90% kelp, 80 to 90% gelatin or kelp and gelatin combined to make 80 to 90% of the total.

In its most preferred formulation, formulation No. 6 containing 50% paprika is preferred with the amount of gelatin and kelp being divided equally to make up the total. Thus, when formulation No. 6 containing 50% paprika, 25% kelp and 25% gelatin, each by volume, was administered at the rate of one-half (½) teaspoon per ten (10) pounds of body weight to dogs and cats, the color intensity of the coat is visibly noticeably different and more highly intensified within a thirty (30) day period. With respect to animals during peak shedding periods when the formulation was added to their diets, it was clear from visual observation that the coat replaced itself at a much faster rate. While the amount of paprika in any given formulation can vary, it has been found in practice that the formulation should have at least 50% by volume in order to obtain optimum results.

While the above invention has been described as containing a formulation of paprika, kelp and a gelatinous material, it should be understood that other materials can be added to the formulation, such as vitamins and minerals, as desired. The amount of these materials added to the formulation can be any amount desirable but is preferably the amount as described by the manufacturer or distrubutor of the material.

I claim:

1. A method of enhancing the color and growth of the coat on mammals selected from the group consisting of felines and canines comprising orally administering one-fourth to one teaspoon per day per ten pounds of body weight of a formulation having at least 50% capsicum tetragonum as a component thereof and the remainder being a mixture of kelp and a gelatinous material.

2. The method as set forth in claim 1 wherein said effective amount is up to one-half teaspoon per day per ten pounds body weight.

* * * * *